United States Patent [19]

Hwang et al.

[11] Patent Number: 4,496,320

[45] Date of Patent: Jan. 29, 1985

[54] CONNECTION OF TRAY TO DENTAL ARTICULATOR

[75] Inventors: Chong S. Hwang, Flushing; Barry Lampert, Lloyd Harbor, both of N.Y.

[73] Assignee: Rab Tec Products Corp., Freeport, N.Y.

[21] Appl. No.: 525,447

[22] Filed: Aug. 22, 1983

[51] Int. Cl.³ .............................................. A61C 11/00
[52] U.S. Cl. ..................................................... 433/60
[58] Field of Search ..................... 433/54, 60, 55, 56, 433/57, 58, 59, 61, 62, 63, 64, 65, 66, 67; 24/265, 264

[56] References Cited

U.S. PATENT DOCUMENTS

| | | | |
|---|---|---|---|
| 530,524 | 12/1894 | Hitch | 433/64 |
| 659,531 | 10/1900 | Johnson | 433/65 |
| 3,120,971 | 2/1964 | Bengtsson | 24/625 |
| 3,390,589 | 7/1968 | Tschanz | 24/625 |
| 4,164,074 | 8/1979 | Lawler et al. | 433/65 |
| 4,252,523 | 2/1981 | Gayso | 433/60 |
| 4,263,715 | 4/1981 | Lampert | 433/60 |
| 4,299,570 | 11/1981 | Yogosawa | 433/62 |
| 4,412,822 | 11/1983 | Blechner | 433/60 |

FOREIGN PATENT DOCUMENTS 2440731  7/1980  France .................................. 433/60

Primary Examiner—John J. Wilson
Attorney, Agent, or Firm—Richard L. Miller

[57] ABSTRACT

An improved connection of tray to dental articulator having a lower jaw and an upper jaw pivotally mounted to the lower jaw and consists of a lower member carried by the lower jaw and an upper member carried by the upper jaw, both members having a female receiving aperture and a dental model tray for each member formed with a male hold-release portion sized to releasably mount within either of the female receiving apertures.

4 Claims, 4 Drawing Figures

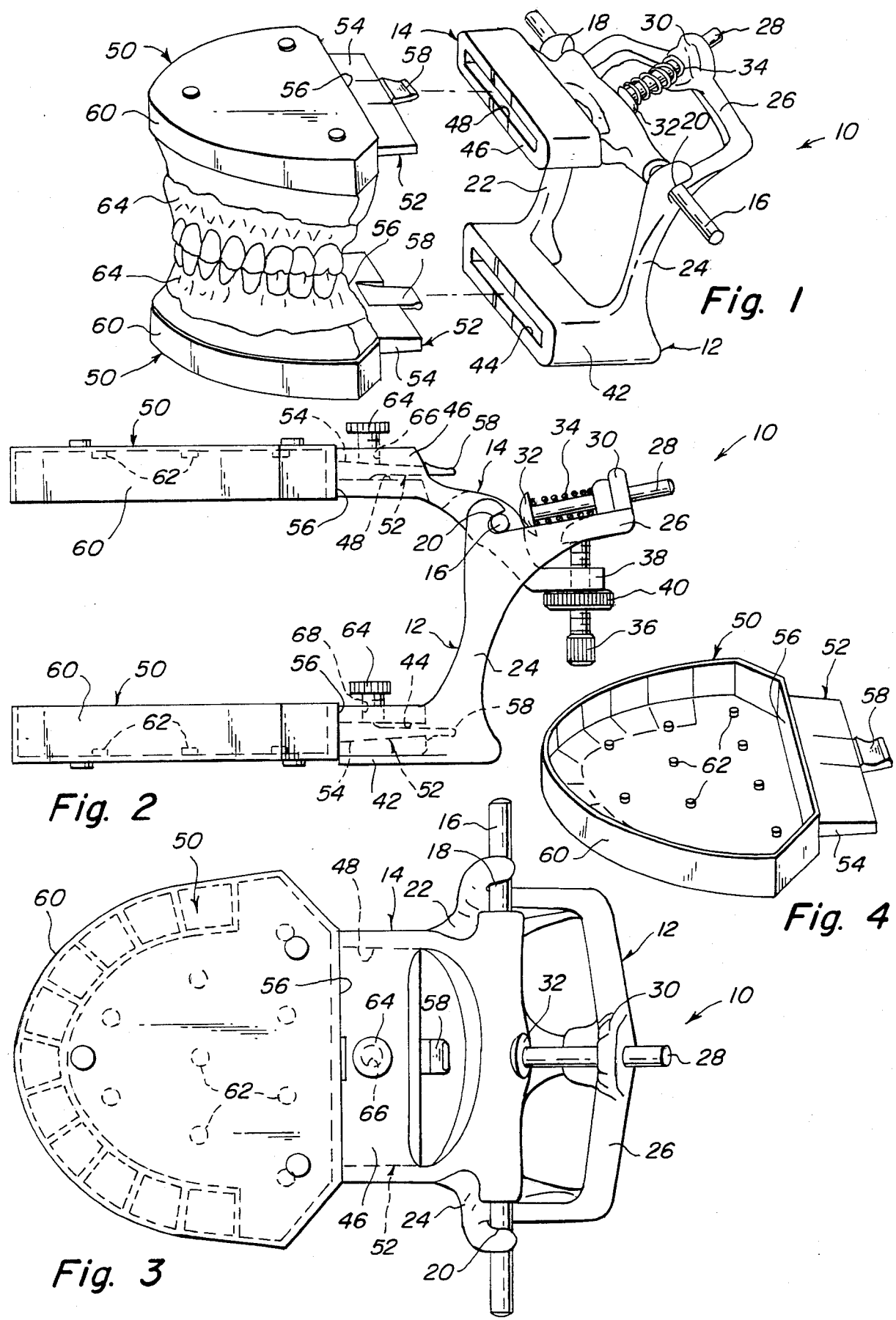

CONNECTION OF TRAY TO DENTAL ARTICULATOR

BACKGROUND OF THE INVENTION

The instant invention relates generally to locking devices and more specifically it relates to an improved connection of tray to dental articulator.

The purpose of this invention is the special interlock and removal of the upper and lower dental model trays from the permanent dental articulator, without the use of complicated clamping devices.

Numerous locking devices have been provided in prior art that are adapted to releasably inter-connect two items. For example, U.S. Pat. Nos. 1,045,586; 3,167,835; 4,207,677; 4,263,715 and 4,319,875 all are illustrative of such prior art. While these units may be suitable for the particular purpose to which they address, they would not be as suitable for the purposes of the present invention as heretofore described.

SUMMARY OF THE INVENTION

A principle object of the present invention is to provide an improved connection of tray to dental articulator consisting of two trays each having a projection that locks into a receiving part in the dental articulator.

Another object is to provide an improved connection of tray to dental articulator whereby either tray with projection can be inserted into upper and lower portion of the dental articulator interchangeably.

An additional object is to provide an improved connection of tray to dental articulator whereby each of the trays retain a dental model for dental restoration work.

A still additional object is to provide an improved connection of tray to dental articulator whereby each tray may be easily released and slipped out of the receiving part in the dental articulator.

A further object is to provide an improved connection of tray to dental articulator that is simple and easy to use.

A still further object is to provide an improved connection of tray to dental articulator that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only and that changes may be made in the specific construction illustrated and described within the scope of the appended claims.

BRIEF DESCRIPTION OF THE DRAWING FIGURES

The figures in the drawings are briefly described as follows:

FIG. 1 is a partially exploded perspective view of the invention.

FIG. 2 is a side view thereof.

FIG. 3 is a top view thereof.

FIG. 4 is a perspective view of a typical dental model tray.

DESCRIPTION OF THE PREFERRED EMBODIMENT

Turning now descriptively to the drawings, in which similar reference characters denote similar elements throughout the several views, FIGS. 1 through 3 illustrates a dental articulator 10 of a somewhat modified construction and design and substantially formed from aluminum or other similar suitable material. A lower jaw member 12 of articulator 10 pivotally mounts an upper jaw member 14 by a pin 16 carried by upper jaw member 14. Pin 16 pivotally rests in seats 18 and 20 formed by notches provided at the junctures of upwardly extending legs 22, 24 of lower jaw member 12 and an arm 26 which extends from both legs 22, 24. A pressure pin 28, slidably disposed in an aperture formed through a boss 30 carried by arm 26 is formed with a head 32 and so as to have a spring 34 wound about its shank and lodged between head 32 and boss 30. Spring 34, when so disposed, urges head 32 of pressure pin 28 against upper jaw 14 to seat pin 16 thereof in seats 18, 20 and maintain upper jaw 14 in pivotal relationship with lower jaw 12.

An externally threaded member, such as a bolt 36, is threaded into an internally threaded boss 38 formed on upper jaw 14 and is fitted with a stop 40. Adjustment of bolt 36 and its co-action with the underside of arm 26 of lower jaw member 12, serves to adjust the position of upper jaw member 14 to lower jaw member 12.

Lower jaw member 12 is formed to include a lower member 42 having a female receiving aperture 44. In similar manner upper jaw member 14 is formed to include a upper member 46 having a female receiving aperture 48. The female apertures 44, 48 both are of the same size, rectangular formed and tapered inwardly form an edge thereof.

As best shown in FIG. 4, a dental model tray 50 is formed from plastic or other suitable material and has a male hold-release portion 52 sized to releasably mount within either of the female apertures 44, 48. The male hold release portion 52 is formed as a rectangular tapered projecting 54 extending outwardly from a back portion 56 of the dental model tray 50 thereof. A semi-flexible central tab 58 extends outwardly from the rectangular projection 54. The tab 58 will flex a little and automatically lock with member 42 or 46 when the male hold-release portion 52 is fully inserted into the female receiving aperture 44 or 48 as shown in FIG. 2. The tab 58 will flex in an opposite direction with a pressure of a finger (not shown) thereby releasing the tab 58 when the male hold-release portion 52 is removed from the female receiving aperture 44 or 48 therefrom.

The tray 50 is shaped like a bow, has a wall 60 around the perimeter and a plurality of small pins 62 within to hold a dental model 64 within (see FIG. 1).

A pair of adjustment screws 64 can also be provided. Each one threadably engages a transverse threaded aperture 66 68 in each member 42, 46. Each adjustment screw 64 will engage a side of the rectangular tapered projection 54 to form a tight fit therein.

The female receiving aperture 44 of the lower member 42 and the female receiving aperture 48 of the upper member 46 are just adequate for the smooth insertion and removal of the male hold-release portion 52 and are sufficiently tight so that the male hold-release portion 52 will not flex either vertically or horizontally. The back edge of the lower member 46 is machined smooth so that the tab 58 of the male hold-release portion 52 will be firmly seated with no forward movement.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. An improved connection of tray to dental articulator having a lower jaw and an upper jaw pivotally mounted to the lower jaw which comprises:
   (a) a lower member having a female receiving aperture, said lower member carried by the lower jaw;
   (b) an upper member having a female receiving aperture, said upper member carried by the upper jaw, wherein the female receiving apertures in said lower and said upper members being of the same size, rectangular formed and tapered inwardly from an edge thereof; and
   (c) a dental model tray for each said member being formed with a male hold-release portion being sized to releasably mount within either of the female receiving apertures, wherein the male hold-release portion being formed as a rectangular tapered projection extending outwardly from a back portion of said dental model tray thereof and having a semi-flexible central tab extending outwardly form said rectangular projection whereby said tab will flex a little and will automatically lock with said member, said male hold-release portion being fully inserted into the female receiving aperture, and whereby said tab will flex in an opposite direction when finger pressure is applied thereby releasing said tab and said male hold-release portion from the female receiving aperture.

2. An improved connecting of tray to dental articulator as recited in claim 1 further comprising a pair of adjustment screws, each threadably engages a transverse threaded aperture in each said member so that said adjustment screw will engage a side of said rectangular tapered projection to form a tight fit therein.

3. An improved connection of tray to dental articulator as recited in claim 2 wherein said dental model tray is formed from plastic.

4. An improved connection of tray to dental articulator as recited in claim 3 wherein said upper member and said lower member of the dental articulator are formed from metal.

* * * * *